(12) United States Patent
Terpstra

(10) Patent No.: US 9,417,125 B2
(45) Date of Patent: Aug. 16, 2016

(54) IR SPECTROMETRY CELL WITH TEMPERATURE CONTROL MEANS

(75) Inventor: Anne Gerben Terpstra, Mantgum (NL)

(73) Assignee: DELTA INSTRUMENTS B.V., Drachten (NL)

( * ) Notice: Subject to any disclaimer, the term of this patent is extended or adjusted under 35 U.S.C. 154(b) by 0 days.

(21) Appl. No.: 14/238,320

(22) PCT Filed: Aug. 3, 2012

(86) PCT No.: PCT/EP2012/065213
§ 371 (c)(1),
(2), (4) Date: Feb. 11, 2014

(87) PCT Pub. No.: WO2013/026677
PCT Pub. Date: Feb. 28, 2013

(65) Prior Publication Data
US 2014/0197334 A1 Jul. 17, 2014

(30) Foreign Application Priority Data

Aug. 24, 2011 (EP) ..................................... 11178585

(51) Int. Cl.
*G01N 21/01* (2006.01)
*G01J 3/02* (2006.01)
(Continued)

(52) U.S. Cl.
CPC .................. *G01J 3/0267* (2013.01); *G01J 3/28* (2013.01); *G01N 21/0332* (2013.01); *G01N 21/05* (2013.01); *G01N 21/3577* (2013.01); *G01N 33/04* (2013.01); *G01N 2021/0346* (2013.01)

(58) Field of Classification Search
CPC ......................................................... B01L 1/00
USPC ......... 250/429, 339.08, 428, 432 R, 435, 437
See application file for complete search history.

(56) References Cited

U.S. PATENT DOCUMENTS 3,869,215 A   3/1975  Nolan
4,415,809 A * 11/1983  Shields .................. G01N 21/03
                                                         250/339.12

(Continued)

FOREIGN PATENT DOCUMENTS

DE       39 18 994        6/1990
EP       1 795 898        6/2007
(Continued)

OTHER PUBLICATIONS

International Search Report for PCT/EP2012/065213 mailed Nov. 13, 2012.
(Continued)

*Primary Examiner* — Jack Berman
*Assistant Examiner* — Jason McCormack
(74) *Attorney, Agent, or Firm* — Nixon & Vanderhye P.C.

(57) ABSTRACT

A sample cell for IR spectrophotometric analysis of a liquid sample is provided. The sample cell comprises two substantially parallel transparent plates enclosing a cavity for holding the liquid sample, and a temperature control loop for controlling a temperature of the liquid sample in the cavity. The temperature control loop comprises at least one temperature sensor for measuring a temperature in or close to the cavity, at least one heating element for increasing a temperature of the liquid sample, and control means, coupled to the temperature sensor and the heating element for controlling the heating element in dependence of the temperature in or close to the cavity. The heating element comprises at least one heating foil which is attached to or thermally coupled to a first one of the transparent plates in such a way to allow an IR light beam to pass through the transparent plates and the cavity without being hindered by the heating foil.

9 Claims, 4 Drawing Sheets

(51) Int. Cl.
*G01N 21/03* (2006.01)
*G01N 21/05* (2006.01)
*G01N 21/3577* (2014.01)
*G01J 3/28* (2006.01)
*G01N 33/04* (2006.01)

(56) References Cited

U.S. PATENT DOCUMENTS

| | | | |
|---|---|---|---|
| 5,092,342 | A | 3/1992 | Hattendorff et al. |
| 6,297,505 | B1 | 10/2001 | Frandsen et al. |
| 2003/0006223 | A1 | 1/2003 | Davis |
| 2005/0211555 | A1* | 9/2005 | Archibald ............... 204/452 |
| 2006/0153742 | A1* | 7/2006 | Shimizu ............... 422/100 |
| 2008/0019881 | A1* | 1/2008 | Fujimoto ............... 422/104 |
| 2009/0154909 | A1* | 6/2009 | Meyer ............... A47J 31/542 392/473 |
| 2011/0147610 | A1* | 6/2011 | Macioszek ........... C12Q 1/6851 250/429 |

FOREIGN PATENT DOCUMENTS

| | | |
|---|---|---|
| GB | 2 223 306 | 4/1990 |
| JP | 2004-206069 | 7/2004 |
| WO | WO 02/096290 | 12/2002 |

OTHER PUBLICATIONS

Written Opinion of the International Searching Authority mailed Nov. 13, 2012.
Tempco Electric Heater Corporation: "Flexible Heaters", Tempco webpage, Apr. 2011, pp. 9-2-9-19, XP002685276.

* cited by examiner

IR SPECTROMETRY CELL WITH TEMPERATURE CONTROL MEANS

This application is the U.S. national phase of International Application No. PCT/EP2012/065213 filed 3 Aug. 2012 which designated the U.S. and claims priority to EP 11178585.3 filed 24 Aug. 2011, the entire contents of each of which are hereby incorporated by reference.

FIELD OF THE INVENTION

This invention relates to a sample cell for IR spectrophotometric analysis of a liquid sample. The sample cell comprises two substantially parallel transparent plates enclosing a cavity for holding the liquid sample and a temperature control loop for controlling a temperature of the liquid sample in the cavity. The temperature control loop comprises at least one temperature sensor for measuring a temperature in or close to the cavity, at least one heating element for increasing a temperature of the liquid sample, and control means, coupled to the temperature sensor and the heating element for controlling the heating element in dependence of the temperature in or close to the cavity.

This invention further relates to the heating element for use in such a sample cell.

BACKGROUND OF THE INVENTION

Such a sample cell is, e.g., known from U.S. Pat. No. 4,415,809 in which an electro-optical apparatus for measurement of fat, protein, lactose and water or solids in milk is disclosed. In this apparatus, a milk sample is pumped into an optical measurement cell and then irradiated with light beams of different wavelengths. The cell comprises a pair of flat parallel optical windows, spaced from each other for containing the sample. The optical windows and the cavity are comprised in a large metal heating block equipped with a temperature sensor, heat resistors and a temperature control circuit.

One of the disadvantages of this setup is that the temperature control loop works too slowly. This leads, for example, to overshoot. When the temperature sensor measures a too low temperature, the heat resistors heat the heating block and the temperature increases over time. When the temperature sensor signals that the desired temperature is obtained, the heat resistors are turned off. The transfer of heat from the heat resistors, through the metal heating block, to the temperature sensor does however take some time. When the temperature at the temperature sensor is right and the heater resistors are turned off, the heat transfer through the metal heating block will not stop immediately. Even when adapting the temperature control loop in order to compensate for this overshoot, it is not possible to keep the sample at the desired temperature.

In the more recent U.S. Pat. No. 6,667,808 the heater element is located closer to the sample cavity, which may reduce the delay between the heater and the sample cavity. However, the use of this single heat source in the larger metal block will always lead to fluctuating temperatures.

OBJECT OF THE INVENTION

It is an object of the invention to improve the temperature stability of the sample cell.

SUMMARY OF THE INVENTION

According to a first aspect of the invention, this object is achieved by providing a sample cell for IR spectrophotometric analysis of a liquid sample, the sample cell comprising two substantially parallel transparent plates enclosing a cavity for holding the liquid sample, a liquid supply channel comprising a first part for pumping fresh liquid into the cavity and a second part for pumping liquid out of the cavity and a temperature control loop for controlling a temperature of the liquid sample in the cavity. The temperature control loop comprises at least one temperature sensor for measuring a temperature in or close to the cavity, at least one heating element for increasing a temperature of the liquid sample, and control means, coupled to the temperature sensor and the heating element for controlling the heating element in dependence of the temperature in or close to the cavity. The heating element comprises at least one heating foil which is attached to or thermally coupled to a first one of the transparent plates in such a way to allow an IR light beam to pass through the transparent plates and the cavity without being hindered by the heating foil.

The use of the heating foil instead of the heating resistors of the prior art gives at least two important advantages. A first advantage is that when the heating foil is attached to the transparent walls of the cavity itself, the source of heat is very close to the liquid to be heated. As a result, the heating of the liquid to be analyzed is much more direct than in the prior art embodiments wherein the metal housing is to be heated first. Because the heating element is closer to the position where the temperature is to be controlled, the heating effect of the liquid is much more direct and temperature fluctuations are reduced.

A further advantage of using the heat foil is that it can easily be provided in any desired shape. For example, a ring shaped heating foil may be used wherein the ring encircles that part of the transparent plate where the IR light beam is to enter (or leave) the cavity. Instead of only heating the sample cell at one or a few positions, the heating element may be designed to heat a larger surface area. This results in a more evenly distributed heat supply and increased control over the temperature of the liquid to be analyzed. Consequently, according to the invention, not only temporal, but also spatial temperature fluctuations are minimized.

It is to be noted that to obtain the above mentioned advantages, it is not absolutely necessary that the heating foil is directly attached to the transparent plate. In principle the invention also works when there is some thermally conductive material in between the heating foil and the transparent plate. However, if there is no good reason for using additional material, the heating foil is preferably attached to the transparent plate itself. The closer the heating foil is to the cavity, the better the temperature control.

The heating foil comprises the temperature sensor. This feature has the advantage that the temperature sensor measures temperatures at a position close to the liquid to be analyzed. The temperature measurement thus provides a more accurate indication of the relevant temperature. With the temperature sensor so close to the heating element, the temperature control loop also becomes faster and thus more accurate. As soon as the temperature starts increasing, the temperature sensor will detect this and the heating element may be turned off. As a result the overshoot in the temperature control loop is minimized.

In addition to the reduced temporal and spatial temperature fluctuations, the invention also improves the reproducibility of the sample temperature. Subsequently analyzed samples therefore have substantially the same temperature or temperature course, which is very important for reliably analyzing multiple samples.

These and other aspects of the invention are apparent from and will be elucidated with reference to the embodiments described hereinafter.

DETAILED DESCRIPTION OF THE INVENTION

Figure 1:
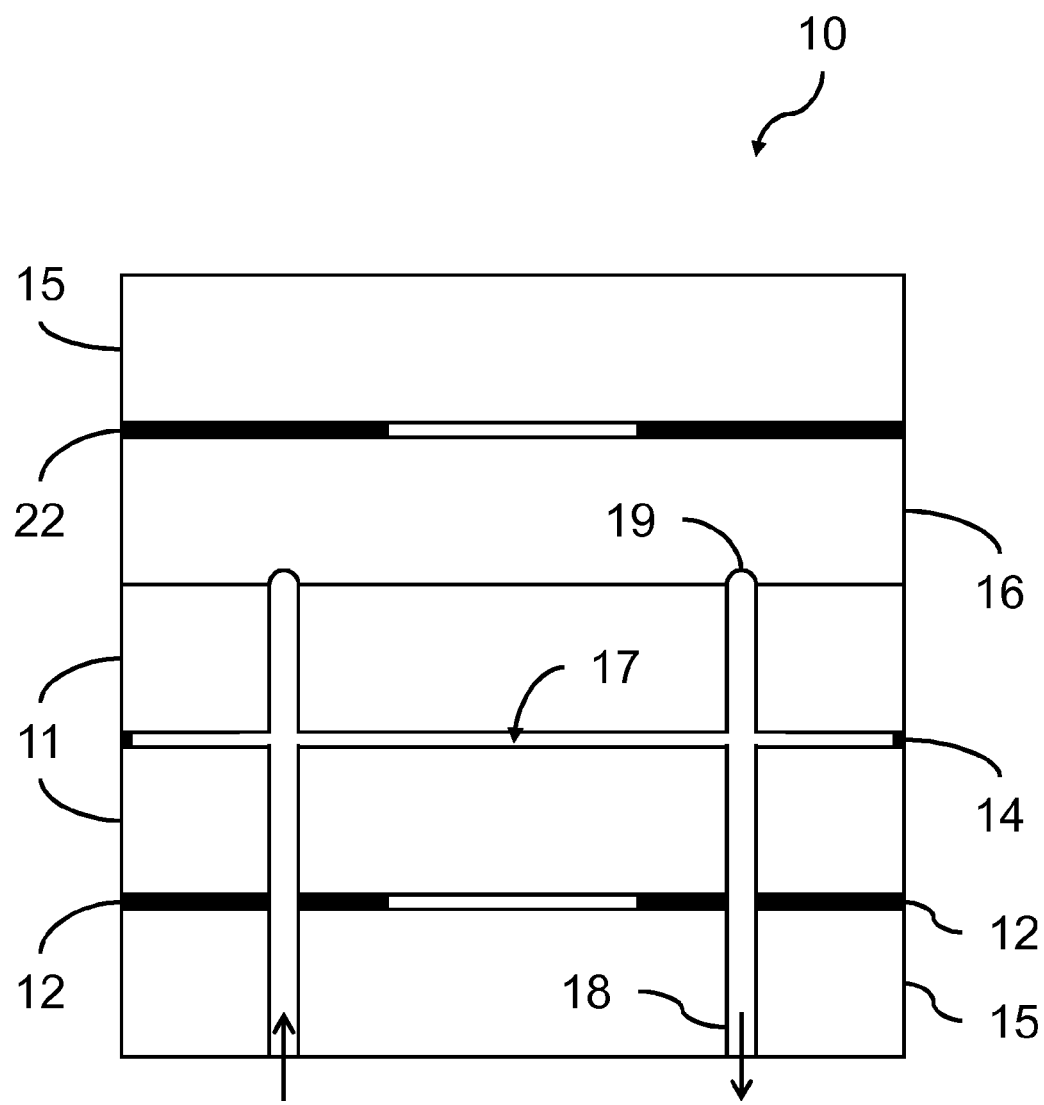
FIG. 1 schematically shows a cross section of a sample cell according to the invention.

FIG. 1 schematically shows a cross section of a sample cell 10 according to the invention. The sample cell 10 comprises two transparent plates 11, separated by spacers 14. In, e.g., milk analysis by IR spectrophotometry the spacers usually provide a 20-40 μm (micrometer) wide cavity 17 between the two substantially parallel plates 11. The transparent plates 11 may, e.g., be made of glass, crystalline calcium fluoride (CaF$_2$) or transparent plastics. Also diamond may be used for producing the sample cell 10. In order to be suitable for IR spectrophotometry, the plates 11 only have to be transparent for the IR wavelengths used for the IR spectrophotometry, but it may be practical to select a material that is also transparent for visible light. If the user can look into the cavity 17, it is possible to visually inspect the analyzed liquid. If the sample cell is also used for analysis methods involving light of a different wavelength, the transparent plates 11 also have to be transparent for said different wavelengths.

A liquid supply channel 18 is provided for enabling the liquid to fill the cavity 17 between the transparent plates 11. Fresh liquid is pumped into the cavity 17 via a first part of the supply channel 18, while used liquid is pumped out of the cavity 17 via a second part of the supply channel 18. The arrows in the figure show a possible direction of flow within the sample cell. When a sample of the liquid is in the cavity 17, the sample can be analyzed, e.g., using IR photospectrometry. When fresh liquid is pumped through the supply channel 18, the cavity 17 is filled with a new sample and a new measurement can be made. In this example, a steel ring 16 is provided comprising a bypass channel 19 for the liquid. The bypass channel 19 is, e.g., ring shaped to provide a bypass from the incoming part of the supply channel 18 to the outgoing part. The bypass channel 19 is provided to prevent excessive pressures caused by the very narrow passage for the liquid in the cavity 17. The steel ring 16 may, of course, also be made of a different metal or thermally conductive material.

A first heating foil 12, preferably with integrated temperature sensors (not visible in this figure), is attached to one of the transparent plates 11. When the temperature sensors are applied to the heating foil 12, the temperature control loop is faster and the liquid sample temperature more stable. The heat foil 12 does not cover the complete surface of the transparent plate 11 in order not to hinder the IR light beam when passing the cavity 17. A second heating foil 22 may be attached to the other transparent plate 11 for further improving the temperature control and increasing the reproducibility of the sample temperature. In this example, the second heating foil 22 is however not attached to the transparent plate 11 itself. For practical reasons, it is attached to the steel ring 16. If the second heating foil 22 was applied between the transparent plate 11 and the steel ring 16, also some sealing would have to be provided for the bypass channel 19.

Although the second heating foil 22 is not attached to the transparent plate directly, it still takes advantage of the inventive idea behind the invention. The diameter of the bypass channel 19 is much bigger than the diameter of the cavity 17. Most of the cold liquid runs through the bypass channel 19. The second heating foil 22 is provided at an excellent position for heating the liquid in the bypass channel 19.

Additional layers 15 of isolating and/or thermally conductive material may be provided. For example, the sample cell 10 may be embedded in a large block of steel that forms a thermal buffer for further stabilizing the temperature at the cavity 17.

Figure 2:
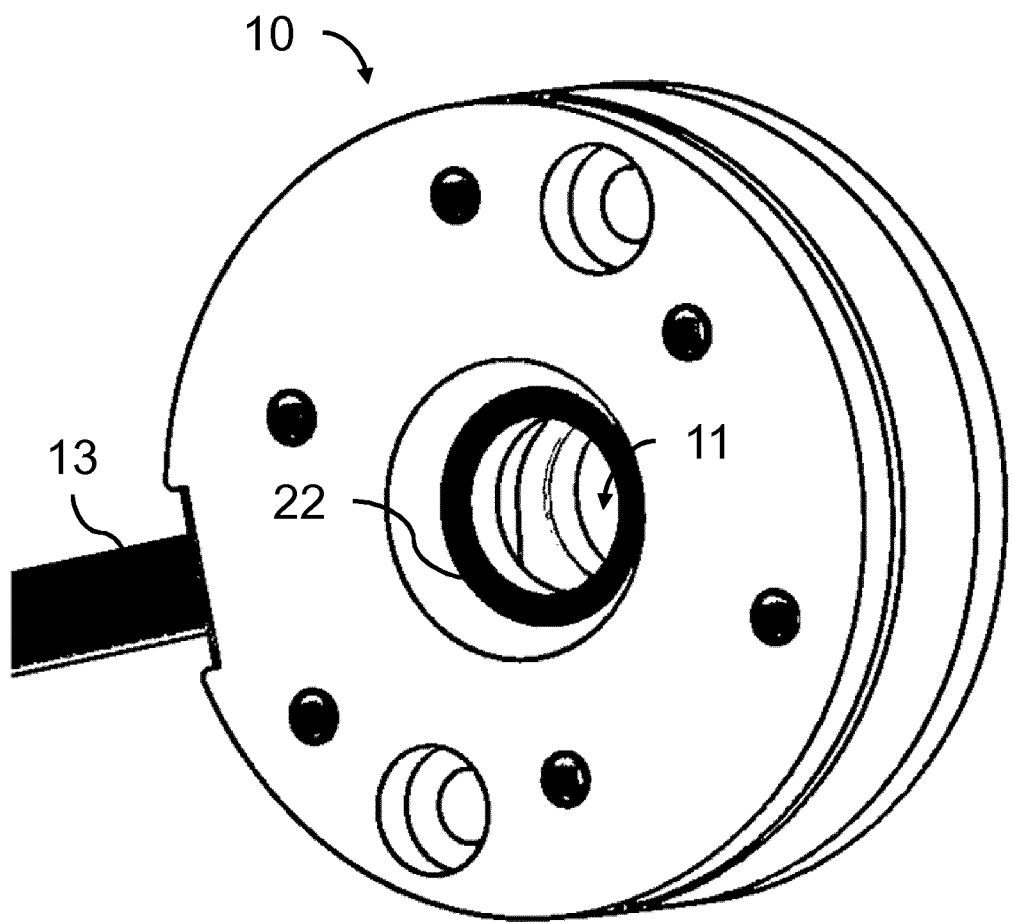
FIG. 2 shows a front view of a sample cell according to the invention.

FIG. 2 shows a front view of a sample cell 10 according to the invention. In this perspective view some of the features described above, with reference to FIG. 1, are shown again. FIG. 2 shows a ring shaped heating foil 22 and the transparent passage for the IR light beam. An incoming IR light beam passes through the ring of the heating foil 22, a first transparent plate 11, the cavity and a second transparent plate 11 before it reaches a detector (not shown). The heating foil 22 is coupled to an electric power source via a connection strip 13. The connection strip 13 preferably is an integral part of the heating foil 22. Also the temperature sensors and the control circuit for controlling the heating means in dependence of the measured temperature may be integrated in the heating foil 22. Alternatively, the temperature sensors and/or the control circuit may be provided separately with an electrical connection to the heating foil 22. If multiple heating foils 12, 22 are used also multiple connection strips 13 may be provided.

Figure 3:
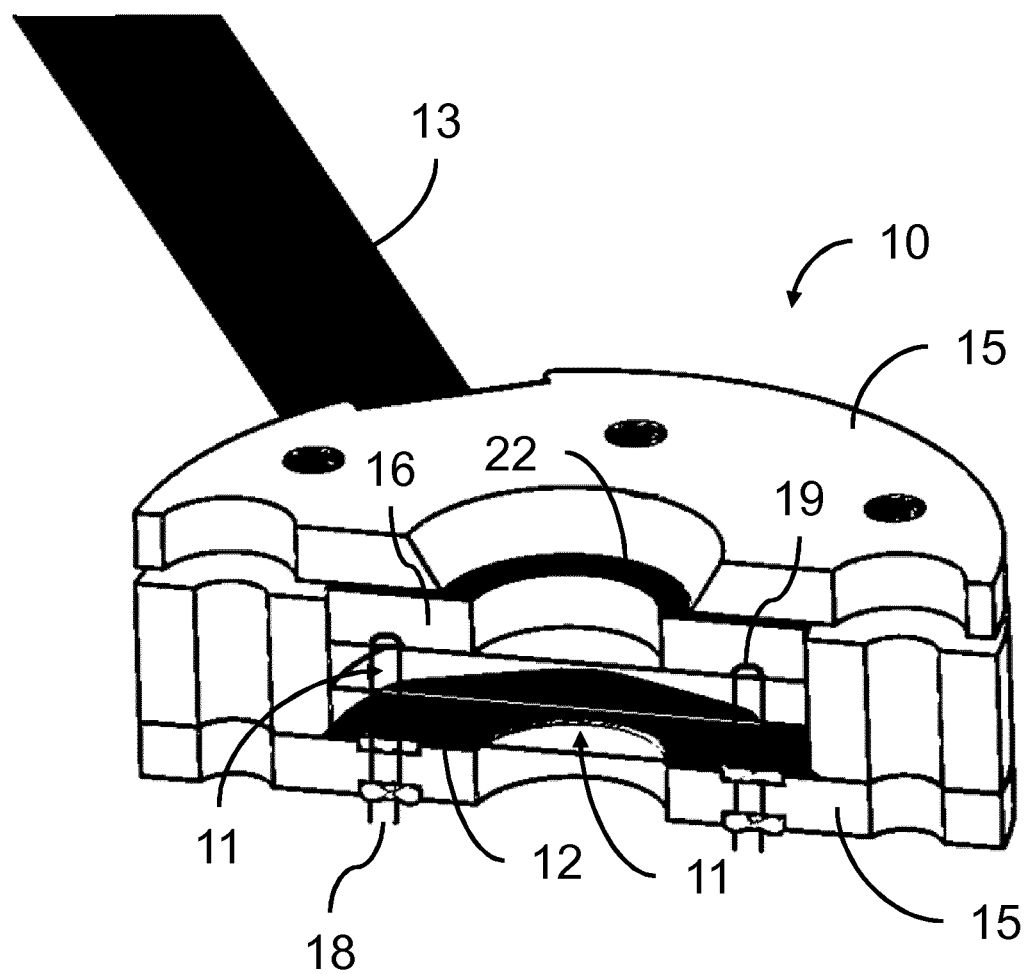
FIG. 3 shows a cross section of the sample cell of FIG. 2, and FIGS. 4a and 4b show two examples of heating foils according to the invention.

FIG. 3 shows a cross section of the sample cell 10 of FIG. 2. The features shown in this figure have already been discussed above with reference to the previous figures.

Figure 4A:
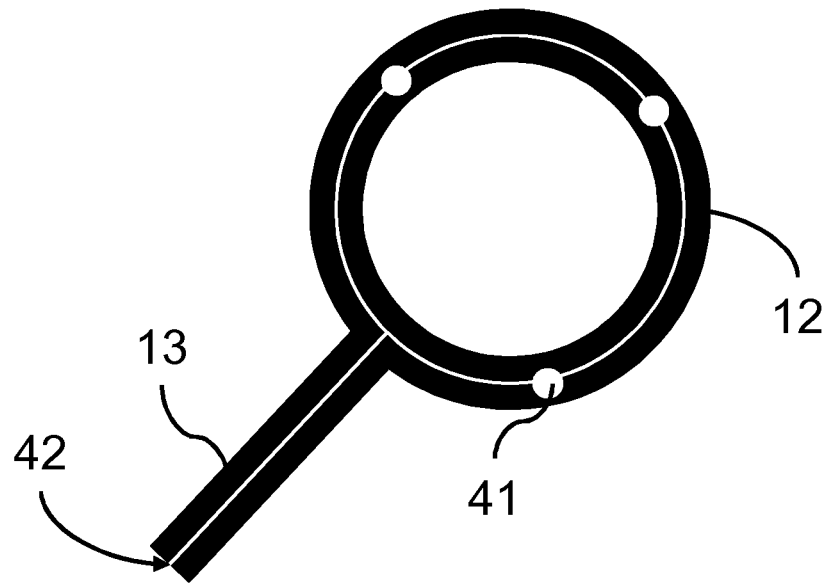
Figure 4B:
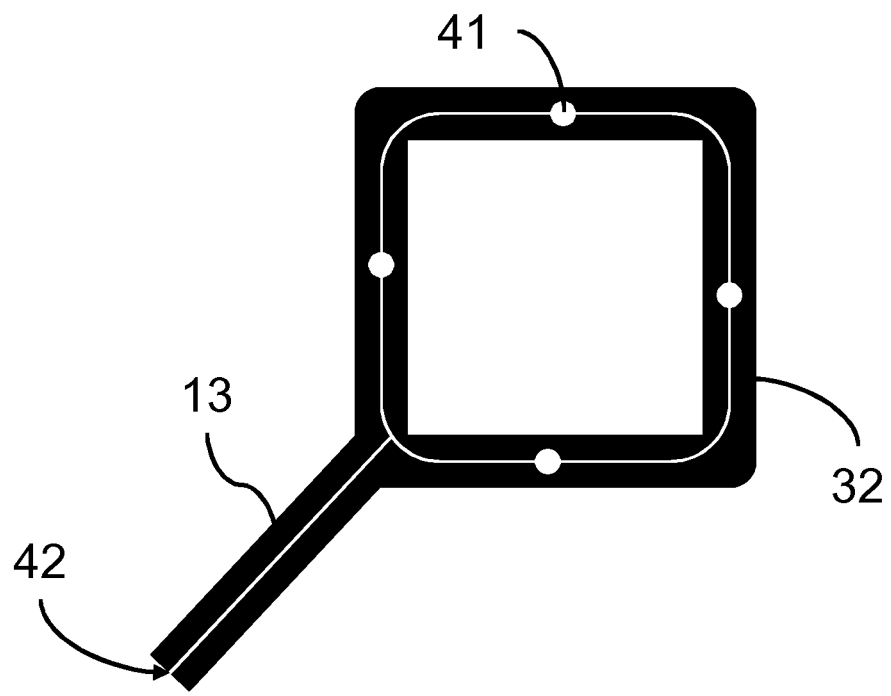

FIGS. 4a and 4b show two examples of heating foils 12, 32 according to the invention. In FIG. 4a, the heating foil 12 is ring shaped. In FIG. 4b, the heating foil 32 is rectangular. Also other shapes may be used. For obtaining the advantages of the current invention, two aspects are important. First, the heating foil 12, 32 must leave open some space for the IR beam to be able to pass through the cavity 17, towards the detector. In addition, the heating foil 12, 32 should cover a significant part of the cavity 17 in order to maximize the heating effect on the liquid inside the cavity 17 and to improve the control over the temperature of different samples. A connection strip 13 may couple the heating foil 12, 32 to a temperature control circuit and/or a power source provided separate from the sample cell 10 itself. The heating foil 12, 32 and the connection strip 13 may, e.g., be made from standard flexible plastic substrates, such as polyimide.

When an electric current runs through the heating foil 12, 32, the electrical resistance of electrical wiring 42 and/or specific heating elements in the heating foil 12, 32 will cause local heating near the foil surface. In addition to electrical wiring 42, the heating foils 12, 32 may comprise one or more temperature sensors 41. For optimal control over the liquid temperature, at least one temperature sensor is provided close to the liquid inlet of the cavity.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A sample cell assembly comprising:
a sample cell for IR spectrophotometric analysis of a liquid milk sample, and
a block of a thermally conductive material in which the sample cell is embedded, the block of the thermally conductive material forming a thermal buffer, wherein
the sample cell comprises:
(a) two substantially parallel transparent plates enclosing a cavity for holding the liquid milk sample,
(b) a liquid supply channel comprising a first part for pumping fresh liquid into the cavity and a second part for pumping liquid out of the cavity,
(c) a bypass channel for providing a bypass from the first part of the supply channel to the second part of the supply channel,
(d) a ring of thermally conductive material which comprises the bypass channel; and
(e) a temperature control loop for controlling a temperature of the liquid milk sample in the cavity, the temperature control loop comprising:
(i) at least one temperature sensor for measuring a temperature in or close to the cavity,
(ii) at least one heating element for increasing a temperature of the liquid milk sample, and
(iii) a controller coupled to the temperature sensor and the at least one heating element for controlling the heating element in dependence of the temperature in or close to the cavity, wherein
the at least one heating element comprises a first heating foil which is directly attached to a first one of the transparent plates in such a way to allow an IR light beam to pass through the transparent plates and the cavity without being hindered by the heating foil, and wherein
the at least one heating element comprises a second heat foil that is directly attached to the ring of thermally conductive material, and wherein
the heating foil comprises the temperature sensor.

2. The sample cell assembly as claimed in claim 1, wherein the thermally conductive material is a metal or steel.

3. The sample cell assembly as claimed in claim 1, wherein the bypass channel is ring shaped.

4. The sample cell assembly as claimed in claim 1, wherein the at least one heating element comprises a second foil which is attached to or thermally coupled to a second one of the transparent plates.

5. The sample cell assembly as claimed in claim 2, wherein the at least one heating element comprises a second foil which is attached to the ring for heating the liquid in the bypass channel.

6. The sample cell ell assembly as claimed in claim 1, wherein the heating foil is ring shaped.

7. The sample cell assembly as claimed in claim 1, wherein
the block of thermally conductive material comprises two plates of a thermally conductive material having an opening, and
the sample cell comprises at least two outward oriented opposite surfaces, one of the two opposite surfaces being formed by a surface of the first one of the transparent plates that faces away from the cavity, the two opposite surfaces being arranged adjacent to the two plates of the thermal buffer and the cavity being arranged in between the openings of the two plates of the thermal buffer, wherein the first heating foil being arranged in between the first one of the transparent plates and a first one of the two plates of the thermal buffer.

8. The sample cell assembly as claimed in claim 7, wherein the ring of the thermally conductive material is arranged in between a second one of the transparent plates and a second one of the plates of the thermal buffer.

9. The sample cell assembly as claimed in claim 1, wherein the ring of the thermally conductive material is arranged in between a second one of the transparent plates and a second one of the plates of the thermal buffer.

* * * * *